United States Patent [19]
Kligerman

[11] Patent Number: 5,989,544
[45] Date of Patent: Nov. 23, 1999

[54] COMPOSITION AND METHOD FOR REDUCING GASTRO-INTESTINAL DISTRESS DUE TO ALPHA-D-GALACTOSIDE-LINKED/CONTAINING SUGARS

[75] Inventor: Alan E. Kligerman, Egg Harbor Township Atlantic County, N.J.

[73] Assignee: Block Drug Company, Inc., Jersey City, N.J.

[21] Appl. No.: 08/487,871

[22] Filed: Jun. 7, 1995

Related U.S. Application Data

[63] Continuation of application No. 08/183,639, Jan. 18, 1994, abandoned, which is a continuation of application No. 07/780,563, Oct. 21, 1991, abandoned, which is a continuation of application No. 07/352,441, May 16, 1989, abandoned.

[51] Int. Cl.$^6$ .................................................. A61K 38/47
[52] U.S. Cl. ...................... 424/94.61; 435/208; 435/267; 426/61
[58] Field of Search ........................... 424/94.61; 426/61; 435/208, 267

[56] References Cited

U.S. PATENT DOCUMENTS

| | | | |
|---|---|---|---|
| 3,493,652 | 2/1970 | Hartman | 424/94.6 |
| 3,632,346 | 1/1972 | Sherba | 426/44 |
| 3,795,585 | 3/1974 | Suzuki et al. | 435/208 |
| 3,846,239 | 11/1974 | Delente et al. | 435/208 |
| 3,966,555 | 6/1976 | Arnaud et al. | 435/208 |
| 3,972,777 | 8/1976 | Yamada et al. | 435/208 |
| 4,241,185 | 12/1980 | Stein et al. | 435/188 |
| 4,259,358 | 3/1981 | Duthie | 426/46 |
| 4,376,127 | 3/1983 | Lunde | 426/46 |
| 4,431,737 | 2/1984 | Olivieri et al. | 435/208 |
| 4,450,238 | 5/1984 | Vitobello et al. | 435/208 |

FOREIGN PATENT DOCUMENTS

| | | |
|---|---|---|
| 0 280 228 A2 | 8/1988 | European Pat. Off. . |
| 48-26978 | 4/1973 | Japan . |
| 50-123870 | 9/1975 | Japan . |
| 57-144982 | 9/1982 | Japan . |
| 58-43075 | 9/1983 | Japan . |
| 1008583 | 10/1965 | United Kingdom . |

OTHER PUBLICATIONS

Solomons et al., "The Efficacy Of An Oral Alpha–Galactosidase To Promote Oligosaccharides Hydrolysis And To Reduce Intolerance Symptoms After Ingestion Of Beans: A Dose–Response Trial" *The American Journal Of Clinical Nutrition*, vol 53, No. 3, p. P–28, 1991.

Ganiats et al., "Does Beano Prevent Gas? A Double–blind Crossover Study of Oral Alpha–Galactosidase To Treat Dietary Oligosaccharide Intolerance" *The Journal Of Family Practice*, vol. 39, No. 5, pp. 441–445, 1994.

Solomons et al., Use Of An Oral Alpha–Galactosidase To Control Gastrointestinal Symptoms From Legume Oligosaccharides In Bean–Intolerant Subjects: A Doubly–Masked, Controlled, Therapeutic Trial, *Clinical Research*, vol. 39, p. 428A, 1991.

Advances In Enzymology, vol. 36, pp. 91–93 (1972).

Suzuki et al., Studies On The Decomposition Of Raffinose by Alpha–Galactosidase Of Mold, *Agr. Biol. Chem.*, vol. 33, No. 4, pp. 501, 507–513 (1969).

*Sugar Technology Reviews*, 4, pp. 209–258 (1976/1977).

*Food Industry and Enzyme*, Published By K.K. Asakura Shoten, pp. 145–150 (Oct. 20, 1983).

*Biochemical Data Book*, Published by Tokyo Chemical Coterie, vol. 1, p. 735, (Nov. 26, 1979).

Solomons et al, Am. J. Clin. Nutr. (1985), 41(2), 209–221, 222–227.

Solomons et al, Am. J. Clin. Nutr. (1985), 41(2), 209–221.

Solomons et al, Am. J. Clin. Nutr. (1985), 41 (2), 222–227.

*Primary Examiner*—Jean C. Witz
*Attorney, Agent, or Firm*—Panitch Schwarze Jacobs & Nadel, P.C

[57] ABSTRACT

A composition is provided for ingestion by mammals for in vivo conversion of alpha-D-galactoside comprising an amount of alpha-galactosidase effective to hydrolyze alpha-D-galactoside to D-galactose, and non-toxic, ingestible excipient(s) for said alpha-galactosidase. Gastric distress in mammals due to ingestion of foods containing alpha-D-galactoside may be reduced by ingesting the foregoing composition of alpha-galactosidase and non-toxic, ingestible excipient contemporaneously with the ingestion of said food in an amount effective to hydrolyze the alpha-D-galactoside to D-galactose.

21 Claims, 1 Drawing Sheet

COMPOSITION AND METHOD FOR REDUCING GASTRO-INTESTINAL DISTRESS DUE TO ALPHA-D-GALACTOSIDE-LINKED/CONTAINING SUGARS

CROSS-REFERENCE TO RELATED APPLICATIONS

This is a continuation of application Ser. No. 08/183,639, filed Jan. 18, 1994, now abandoned, which in turn is a continuation of application Ser. No. 07/780,563, filed Oct. 21, 1991, now abandoned which in turn is a continuation of application Ser. No. 07/352,441, filed May 16, 1989, now abandoned.

FIELD OF THE INVENTION

The present invention relates to the improved digestion of certain foods and prevention of gastrointestinal distress and other symptoms associated with these foods. More particularly, the invention relates to a composition and method for reducing gastrointestinal symptoms in mammals due to ingestion of foods containing alpha-D-galactoside-linked sugars.

BACKGROUND OF THE INVENTION

The ingestion of certain foods by mammals results in flatulence and/or other gastrointestinal symptoms. Certain foods that are extremely flatugenic include milk and milk products, legumes (e.g., peanuts, beans), some cruciferous vegetables (e.g., cabbage, brussels sprouts) and certain fruits (e.g., raisins, bananas, apricots). See Rackis, J. J., "Flatulence Caused by Soya and Its Control through Processing," *JAOCS*, page 503 (1981). The primary cause of flatulence from the previously mentioned foods is the body's inability to digest certain carbohydrates contained within these foods. The mammalian inability to digest these carbohydrates allows putrefactive bacteria in the large intestine to break down these carbohydrates by fermentation. This results in the formation of excessive levels of rectal gas, primarily carbon dioxide, methane and hydrogen.

The mammalian ability or inability to digest certain carbohydrates depends upon the presence or absence of certain enzymes in the digestive system and the type of carbohydrate to be digested. For example, the human being's ability to secrete the specific enzyme enabling him or her to digest the carbohydrate, lactose (commonly called "milk sugar"), depends upon a number of factors, e.g., age, race and health. Beta-D-galactoside-galactohydrolase (commonly called "beta-galactosidase" or "lactase") is secreted within a human being's digestive system in order to hydrolyze lactose (a molecule which contains the beta-galactoside linkage) into its digestible monosugars, glucose and galactose. When beta-galactosidase activity is not present in sufficient quantities in order to hydrolyze lactose, in vitro treatment of milk or oral administration of microbial beta-galactosidase(s) for in vivo use duplicates the function of the naturally occurring neutral intestinal beta-galactosidase found on the gut wall (known as intestinal lactase).

Lactaid Inc. of Pleasantville, N.J., has been providing a beta-galactosidase in various forms, since approximately 1974, for the in vitro and in vivo treatment of milk. In vitro treatment of milk with beta-galactosidase was first performed by the consumer at home. Approximately ten years ago, in vitro treatment of milk was done on a commercial scale by the dairy industry. Since approximately 1984, a beta-galactosidase preparation has been available on a substantial scale by a number of companies, including Lactaid Inc., for in vivo use.

The success of an ingestible form of beta-galactosidase for in vivo use was not entirely surprising, since the ingested enzyme structurally and functionally duplicates beta-galactosidase present within the human digestive system. There was initial concern as to whether an ingested form of beta-galactosidase subject to varying pH levels would operate effectively in the human stomach and/or intestine. The fact that certain dosages of oral beta-galactosidase preparations did indeed substantially digest dietary lactose in the stomach and small intestine of persons lacking the natural form of this enzyme showed that at least some enzymes from microbial sources were not inactivated by the conditions of acidity, protein digestion, temperature or motility found in the gastrointestinal tract.

The lactose of milk and milk products is digestible by essentially all mammals during at least part of their lives. But this is not the case with certain sugars contained in legumes and certain fruits. The above-mentioned flatugenic legumes, vegetables, and fruits contain one or more of the carbohydrates: raffinose, stachyose and verbascose. What these three oligosaccharide molecules all have in common is a D-galactose sugar linked to another sugar unit via an alpha-galactoside linkage. Enzymes of the class alpha-D-galactoside-galactohydrolase (commonly called "alpha-galactosidase") have the capacity to hydrolyze this alpha-galactoside sugar linkage. D-galactose is a monosaccharide which can be absorbed by the intestinal cell into the body and thereafter converted to glucose. Humans and other mammals cannot digest the three oligosaccharides to liberate D-galactose, since their digestive systems do not produce alpha-galactosidase.

In vitro use of alpha-galactosidase to render the previously-mentioned oligosaccharides digestible is well known. U.S. Pat. Nos. 3,966,555; 4,241,185; and 4,431,737 disclose methods of producing and/or stabilizing alpha-galactosidase by culturing of various microorganisms. All that these patents disclose or imply is that alpha-D-galactosidase can be used in vitro in food processing and/or by addition to foodstuffs for a period of up to 12 hours. This demonstrates the ability to hydrolyze, in vitro, alpha-D-galactoside-linked sugars.

Further, it is well known to use industrial food processing methods for in vitro hydrolysis of alpha-D-galactoside-linked sugars with the addition of alpha-galactosidase. See Cruz, R. et al. "Microbial alpha-Galactosidase for Soy Milk Processing", 46 Journal of Food Science 1196–1200 (1981). Soaking, fermentation, enzymatic hydrolysis, and germination can also be used to eliminate or digest oligosaccharides. Tests with humans and rats indicate that a combination of such in vitro processes can be used to reduce flatus production. See Rackis, J. J., supra. Also well known in the art is that a technique frequently used in commercial processing, namely canning, increases the in vitro rate of hydrolysis of starch and legumes. See Traianedes, et al., "Commercial Canning Increases the Digestibility of Beans in Vitro and Postprandial Metabolic Response to Them in Vivo", *The American Journal of Clinical Nutrition* 44: Sep. 1986, pp. 390–397.

There are many problems associated with the in vitro processing of foods containing alpha-D-galactoside-linked sugars with the enzyme alpha-galactosidase in order to hydrolyze said alpha-D-galactoside-linked sugars and thus reduce symptoms in mammals ingesting them. The treatment of intact (unmacerated or unchewed) beans or other vegetables and fruits by an enzymatic means is inefficient and costly. The solid nature of these foods precludes efficient, uniform and effective enzyme activity. Solid foods can be turned into a slurry first for more effective enzyme treatment, but this is time-consuming and sometimes non-appetizing, as it prevents serving the food in its original form.

To applicant's knowledge, no one has ever proposed or attempted the feat of delivering an effective alpha-galactosidase orally for in vivo digestion of raffinose, stachyose or verbascose.

SUMMARY OF INVENTION

According to the present invention, a composition is provided comprising an effective mount of alpha-galactosidase and non-toxic, ingestible excipient(s) in order to hydrolyze alpha-D-galactoside-linked sugars in vivo. The composition may also contain potentiating agent(s) for the alpha-galactosidase. The flatulence and/or other subjective gastrointestinal symptoms in mammals due to the fermentation of the oligosaccharides contained in foods may be reduced or eliminated by ingesting (orally) alpha-galactosidase enzymes along with said foods. Also markedly reduced or eliminated is objectively measured gastric hydrogen production, a post-meal upsurge of which is prima-facie objective evidence of maldigestion. The alpha-galactosidase-containing composition may be orally ingested alone in various forms immediately before, during or immediately after ingestion of the food, or mixed with the food. For in vivo activity of alpha-galactosidase to be most effective, the composition should be ingested during a time period from about one-quarter hour before to about one-quarter hour after ingestion of the alpha-D-galactoside-containing food, although ideally, composition ingestion should be instantly before and/or during the meal.

DETAILED DESCRIPTION OF THE PREFERRED EMBODIMENTS

Figure 1A:
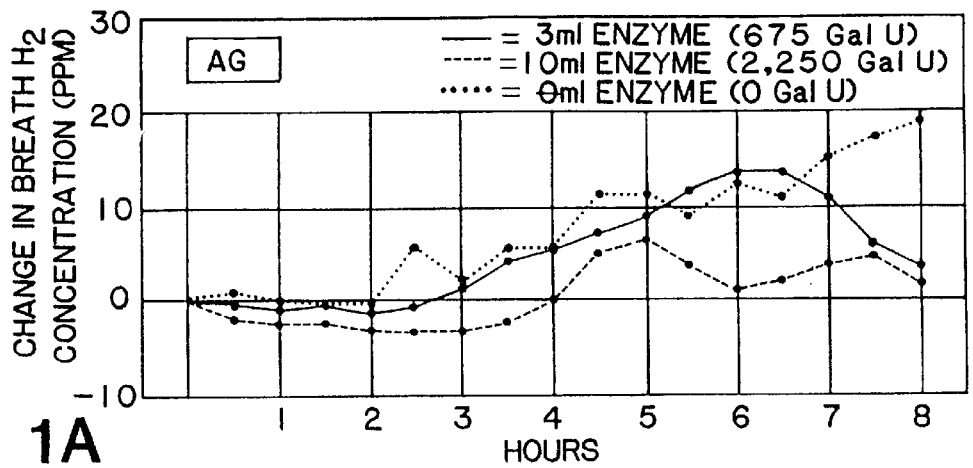
FIGS. 1A, 1B and 1C are a set of graphs which demonstrates the change in $H_2$ concentration of subjects' breath for 3 sets of tests, each set comprising three tests, as a function of the testing time period. A more detailed explanation is contained in the Experimental Examples section below.

The composition comprising alpha-galactosidase and non-toxic excipient(s) (ingestible composition) can be ingested in a wide variety of forms such as a powder for combining with food via sprinkling on or mixing in, or as a liquid, tablet, capsule or soft-gel capsule. Food grades of alpha-galactosidase can be obtained in the form of a liquid or powder from, among others, Novo Industri A/S, Novo Alle, 2880 Bogvaerd, Denmark, with U.S. offices in Danbury, Conn.

Alpha-galactosidase is generally provided in powdered form and may be combined with one or more excipients, which are also in powdered form, to produce solid forms of the ingestible composition, i.e., tablet, capsule, powder. Concentrated (highly pure) liquid alpha-galactosidase may be formed into an ingestible powdered composition thus: a liquid form of alpha-galactosidase is absorbed and/or adsorbed by dry powder excipient(s), diluted and evenly dispersed throughout the tablet or capsule preblend. Liquid forms of alpha-galactosidase can also be utilized for taking orally in soft-gel capsule form, or for administration by drops or by spoon from a bottle; or for application directly to food just prior to eating by drops onto the food or mixed with the food. In such cases, the liquid is diluted with other appropriate diluent liquids or excipients. The degree of dilution will depend on the use intended; very little dilution for liquid gel capsule use and substantial dilution for preprandial addition directly to foods.

Representative examples of dry ingredients that can be combined with a food grade alpha-galactosidase to form the ingestible composition include but are by no means limited to: dextrose, dicalcium phosphate, microcrystalline cellulose, modified cellulose and modified starch. Representative examples of liquid excipients include but are by no means limited to: water, glycerol and sorbitol. These excipients are available from normal trade sources. Important criteria for selecting these excipients, besides their function as ingestible non-toxic carriers of the enzyme alpha-galactosidase, are their palatability, ease of flow into capsules and/or good qualities of tablet compressibility for dry uses, and miscibility, stabilization qualities and taste, for liquid uses.

Generally, commercially available alpha-galactosidase in liquid form contains about 225 alpha-galactosidase units (GalU) per milliliter. Since there is at present no "weight" standard for this enzyme, GalU will be the sole unit or standard of alpha-galactosidase strength used throughout this disclosure. A "pure" enzyme is impractical because of commercial production purification limitations. 1 GalU=the amount of alpha-galactosidase required to form 1 micromole of p-nitro phenol+galactose from p-nitrophenyl alpha-D-galactopyranoside in one minute under standard test conditions of pH 4.5 at 37° C.

The ingestible composition may contain other excipients than those previously mentioned, if they have a similar function. For example, where the ingestible composition is in tablet form, hydrogenated vegetable oil is generally required as an incidental additive, functioning as a lubricant in the tablet-stamping process. A preferred composition for any of the above-mentioned forms contains several excipients.

Dosages per average meal of flatus producing food wherein the alpha-galactosidase is present in an amount below 675 GalU have been found to be somewhat effective for most people, although this may be enough for "marginal" flatus/symptom producers. Amounts above 31,000 GalU per meal are generally wasteful levels, but may still be required by the truly high gas producer. These high levels are otherwise physiologically harmless, except for the possible rare allergy.

Ingestion of a composition comprising an effective amount of alpha-galactosidase in a non-toxic ingestible excipient, substantially simultaneous or contemporaneous with the ingestion of foods containing alpha-D-galactoside-linked sugars, results in the complete or partial hydrolysis of these oligosaccharides into their simplest absorbable constituents, in vivo. The time period for ingesting the alpha-galactosidase containing composition is preferably from about ¼ hour before to about ¼ hour after ingestion of foods containing the alpha-D-galactoside-linked sugars. Effectiveness can be expected to decrease appreciably with increasing time displacement of the alpha-galactosidase ingestion from the time of the meal because, to be effective, the enzyme must mix in the stomach with the foods ingested, so must arrive there more or less simultaneously with the food. The most preferred time to ingest the alphagalactosidase-containing composition is simultaneous with the alpha-D-galactoside-linked sugars-containing foods.

The enzyme can be delivered in the form of a tablet, soft-gel capsule or similarly shaped pill in ingestible form, although plain liquid can be used as mentioned earlier. Also, a powdered form of the ingestible composition which is packeted or kept on the table in a "salt-shaker" can be sprinkled on the food, or a liquid form, such as that administered from a bottle, can easily be orally taken as the food is eaten, or mixed with the food immediately prior to eating. Such immediate prior mixing is not an in vitro use, but a version of in vivo use, with "immediate" meaning any time from "in the plate on the table" to several hours prior mixing, since the enzyme activity will be in vivo, not in vitro, in any solid food.

Oral administration is just one way of supplying the enzyme to the digestive system. The ingestible composition could be administered through a tube or similar device which is connected to the stomach or small intestine. Furthermore, this invention is suited for various types of mammals and is not just limited to use in human beings. For example, one may find this invention particularly suited for pets, such as dogs or cats, who often experience symptoms and emit noxious odors associated with flatulence after they have ingested alpha-D-galactoside-linked sugar-containing foods.

The invention will now be illustrated in more detail by reference to the following specific, non-limiting examples:

EXPERIMENTAL EXAMPLES

To permit quantitative evaluation of the effectiveness of the method of using alpha-galactosidase compositions to reduce gastrointestinal symptoms in mammals due to fermentation of gas-producing foods, a series of tests on humans was performed.

Each test involved a standard meal of 230 grams of refried, mashed, black beans served with unsweetened coffee at the beginning of the experiment. This quantity of cooked beans is estimated to contain about 5 grams of alpha-D-galactoside-linked oligosaccharides. Samples of expired air were collected at zero-time (at the beginning of the experiment), and at 30 min. intervals, for a total of 16 intervals over an 8-hour period from 3 subjects who ingested the standard meal. After the fourth hour, the subjects received a meal of a rice pudding made with lactose-hydrolyzed milk, since both rice starch and lactose-hydrolyzed milk produce a negligible hydrogen gas ($H_2$) signal. The subjects were interviewed regarding symptoms they experienced during the 8-hour period and symptoms were reported and tabulated. The subjects were aware of ingesting the enzyme preparation and its purpose. Table 1 shows the symptoms that were reported.

The tabulated subjects (designated "A", "B" and "C") individually underwent a total of nine tests; three identical tests at these volumes of enzyme preparation per meal: 0, 3 ml and 10 ml. The first set of three tests involved just the ingestion of the standard meal. The second set of three tests involved the standard meal ingested contemporaneously with 3 ml (675 GalU) of the liquid enzyme preparation. The third set of three tests involved the standard meal ingested contemporaneously with 10 ml (2250 GalU) of the liquid alpha-galactosidase preparation. Enzyme was mashed into the beans and was eaten with them. In all cases the enzyme was mixed in with the meal immediately prior to consumption.

Figure 1B:
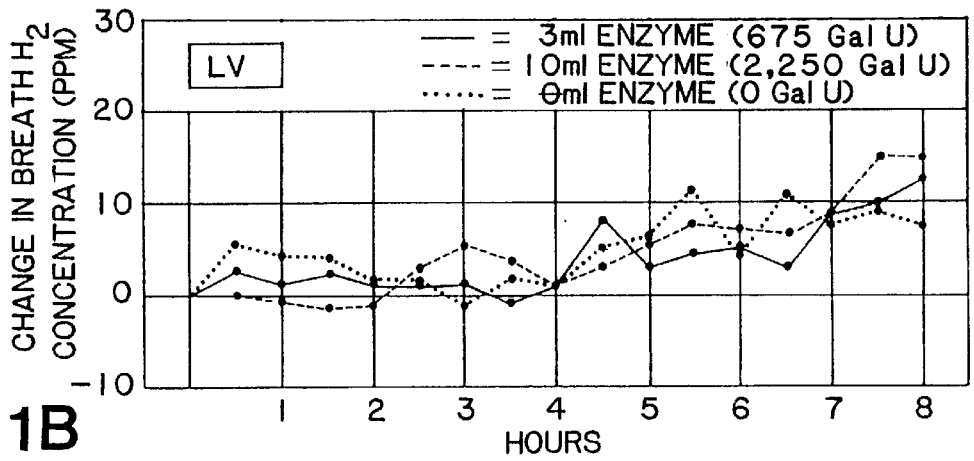
Figure 1C:
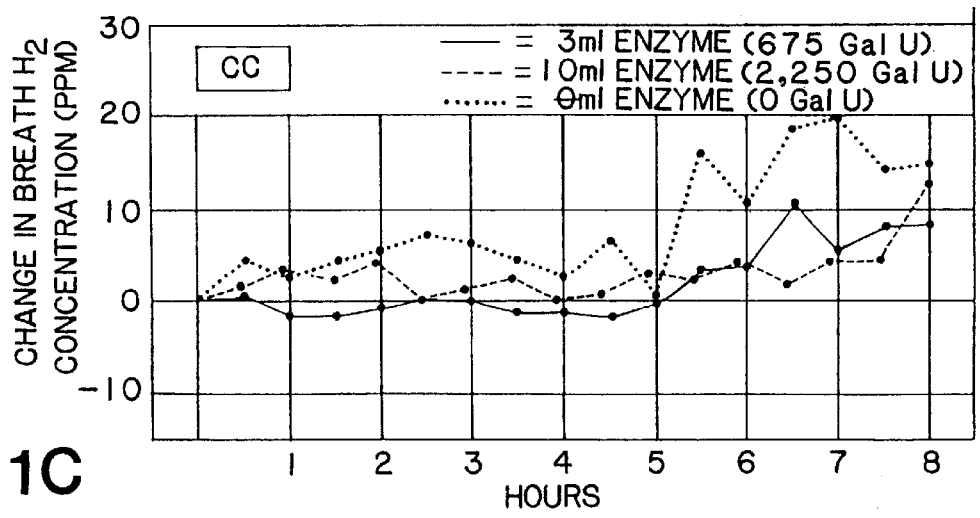

FIG. 1 shows graphs where three individual curves represent the data collected for each subject and indicate the changes in concentration of $H_2$ in the breath of these subjects during the eight hour testing period. The data points represent the average breath hydrogen concentration at each of the 30 minute time intervals following the ingestion of the bean meal relative to the zero-time $H_2$ reading (i.e. averaged actual $H_2$ reading minus zero-time $H_2$ reading) and are represented on the horizontal axis. Each curve represents the average change in the concentration of $H_2$ over the eight hour test periods for the three tests for each individual's set.

The curves indicating changes in the $H_2$ concentration when the subjects ingested one of the enzyme preparations are generally lower than the curves representing changes in $H_2$ concentration when the subject did not ingest the enzyme. The lack of significant changes in all subjects, all tests, over approximately the first 5 hours is expected as this is the period during which the meal travels from the mouth to the lower intestine which is where the $H_2$ is generated. The rise in hydrogen output during the final hours of observation is in response to gas formation due to fermentation of carbohydrates in the lower intestine.

Table 1 shows the cumulative sum of the changes (relative to zero-time reading) of $H_2$ concentration of subjects' air as a function of the amounts of enzyme preparation ingested by the subjects with the standard meal (approximating the integral or area under curve). Column ABC presents the data compiled for all the subjects. Columns A, B and C, respectively, present the data compiled for subjects "A", "B" and "C", individually. Median values for cumulative change calculated for all the subjects are presented in column ABC; they are respectively: 127 parts per million (hereinafter "ppm") of $H_2$ resulting from the ingestion of beans alone; 77 ppm of $H_2$ resulting from the ingestion of beans with 3 ml (675 GalU) of the enzyme preparation; and 39 ppm of $H_2$ resulting from the ingestion of beans with 10 ml (2250 GalU) of the enzyme preparation.

Columns A, B and C show the sets of the tests for each of the individual subjects. The results indicate that including the enzyme preparation with the standard meal lowers the amount of gas produced by the formation of non-hydrolyzed alpha-D-galactoside-linked sugars. In 14 of the 18 instances in which the enzyme preparation was ingested with the standard meal, the $H_2$ concentration was below the range resulting from the meals without the enzyme preparation. These data suggest that effective amounts of the enzyme preparation can reduce $H_2$ gas production that is associated with non-hydrolyzed alpha-D-galactoside-linked sugars within the digestive tract.

Also impressive was the effect of enzyme-ingestion on the subjective symptom response (Table 2). As a result of ingestion of the standard meal alone, subjective symptoms were experienced on 6 of 9 occasions. On ingestion of the standard meal with 10 ml (2250 GalU) of the enzyme preparation no symptoms were experienced.

It was noted that at the 3 ml dosage, the taste of the enzyme preparation was imperceptible. At the 10 ml (2250 GalU) dosage, a salty taste was experienced. Therefore, the practical use of the enzyme would not be precluded even though it might be less palatable. Also, as more purified forms of enzyme are obtained, the off-tastes can be expected to be reduced or eliminated. In tablet, capsule, liquid or mixed-with-food forms, the unpalatability would be minimized in any case.

TABLE 1

THE CUMULATIVE SUM OF CHANGES IN $H_2$ CONCENTRATION OF SUBJECTS BREATH PPM CLINICALLY MEASURED SYMPTOMS

| Average For Three Tests | Enzyme Preparation (ml) | ABC (Combined) (Median Value) | A | B | C |
|---|---|---|---|---|---|
| 1 Set | 0 | | | | |
| 1st | " | | 142 | 95 | 209 |
| 2nd | " | | 123 | 90 | 144 |
| 3rd | " | 127 | 120 | 77 | 78 |
| 2 Set | 3 ml | | | | |
| 1st | " | | 104 | 147 | 127 |
| 2nd | " | | 101 | 53 | 74 |
| 3rd | " | 77 | 78 | 5 | −47 |
| 3 Set | 10 ml | | | | |
| 1st | " | | 27 | 128 | 147 |
| 2nd | " | | 22 | 67 | 39 |
| 3rd | " | | 6 | 57 | −22 |

TABLE 2

SUBJECTIVE SYMPTOMS

| Subject A | | | Subject B | | | Subject C | | | Amount of |
|---|---|---|---|---|---|---|---|---|---|
| 1 | 2 | 3 | 1 | 2 | 3 | 1 | 2 | 3 | Enzyme |
| Abd. pain | flatulence | flatulence | No Symptoms | flatulence | Abd. pain | No Symptoms | No Symptoms | flatulence | Alone |
| Flatulence | Belching Gas | No Symptoms | belching | belching gas flatulence | No Symptoms | No Symptoms | flatulence | No Symptoms | 3 ml Enzyme |
| No Symptoms | No Symptoms | No Symptoms | No Symptoms | No Symptoms | No Symptoms | No Symptoms | No Symptoms | No Symptoms | 10 ml Enzyme |

FORMULATION EXAMPLE

This example concerns the invention in the form of a tablet. A typical tablet will weigh approximately 450 mg (but this size is only exemplary and not restrictive; the tablet or capsule can easily be appreciably larger or smaller) and contain approximately 675 GalU of alpha-galactosidase depending on the standardized strength of that particular batch of enzyme. In this case, a food grade alpha-galactosidase was obtained in the form of a liquid from Novo Industri A/S. Assuming a 675 GalU presence of enzyme, the following excipients will typically be included, however, the following proportions are simply examples and are not rigid:

TABLE 3

EXCIPIENT FORMULATION FOR TABLETS

| Excipient | Amounts (mg) | Form | Obtained From |
|---|---|---|---|
| Dextrose | 177 | Powder | Edw. Mendell Co. |
| Dicalcium Phosphate | 129 | Powder | E. M. Sargent Co. |
| Microcrystalline cellulose | 39 | Powder | FMC Corp. |
| Modified cellulose | 21 | Powder | FMC Corp. |
| Modified starch | 19 | Powder | Colorcon, Inc. |
| Hydrogenated vegetable oil | 19 | Powder | Edw. Mendell Co. |

A larger presence of enzyme will not necessarily require a larger tablet or capsule; the excipients can be adjusted downward (or upwardly) as necessary by changing the amount of dextrose (bulking agent), for example. The hydrogenated vegetable oil does not aid in the ingestion of the enzyme alpha-galactosidase, but functions solely as a lubricant in the tablet-stamping process.

Also, certain potentiating agents are available, by use of which the requirement for enzyme may be reduced, lowering the bulk of active ingredient required as well as the cost of the finished product. An example of one such agent is a blend of carbohydrases including arabanase, cellulase, and xylanase. It is sold under the trade name "Viscozyme 120 L" by Novo Laboratories of Danbury, Conn. In our experiments to remove raffinose and stachyose, we noted that both alpha-galactosidase and the Viscozyme 120 L work optimally at pH 4.5. The ideal ratio of alpha-galactosidase to Viscozyme 120 L varies over the range:

0.19% alpha-galactosidase/1.5% Viscozyme 120 L
to
1.0% alpha-galactosidase/1.5% Viscozyme 120L
when added on a w/w percent basis to as is soybean meal (90% dry solids).

The present invention may be embodied in other specific forms without departing from the spirit or essential attributes thereof and, accordingly, reference should be made to the appended claims, rather than to the foregoing specification as indicating the scope of the invention.

What is claimed is:

1. A method of reducing gastric distress in mammals due to ingestion of solid food containing alpha-D-galactoside-linked sugars, comprising ingesting a composition of alpha-galactosidase and a non-toxic ingestible excipient for said alpha-galactosidase, said composition being in tablet or soft-gel capsule form containing an amount of alpha-galactosidase effective to hydrolyze said sugars in vivo to their simplest absorbable constituents, the ingesting of the composition being contemporaneous with the ingestion of the solid food containing said sugars, wherein the alpha-galactosidase hydrolyzes the food in vivo after mixing in the stomach of the mammal ingesting the food.

2. The method according to claim 1, wherein the alpha-galactosidase is ingested during a time period from about ¼ hour before to about ¼ hour after ingestion of the alpha-D-galactoside-containing food.

3. The method according to claim 1, wherein said composition is administered to yield an amount of about 675 to 31,000 GalU per average flatugenic meal.

4. The method according to claim 1, wherein said composition is ingested in tablet form.

5. The method according to claim 4, wherein at least one tablet is ingested prior to the ingestion of the food.

6. The method according to claim 4, wherein at least one tablet is ingested during the ingestion of the food.

7. The method according to claim 1, wherein said composition is ingested in soft-gel capsule form.

8. The method according to claim 7, wherein at least one capsule is ingested prior to the ingestion of the food.

9. The method according to claim 7, wherein at least one capsule is ingested during ingestion of the food.

10. The method according to claim 1, wherein said alpha-galactosidase is optimally effective at a pH of about 4.5.

11. The method according to claim 1, wherein said solid food is intact prior to ingestion.

12. The method according to claim 1, wherein said solid food is selected from the group consisting of fruits and vegetables.

13. The method according to claim 13, wherein said solid food comprises beans.

14. The method according to claim 1, wherein said composition further comprises an agent for potentiating said alpha-galactosidase.

15. The method according to claim 14, wherein said potentiating agent comprises a blend of carbohydrases including arabanase, cellulase and xylanase.

16. The method according to claim 1, wherein the mammal is a human being.

17. A method of reducing gastric distress in mammals due to ingestion of solid food containing alpha-D-galactoside-linked sugars, comprising ingesting a composition of alpha-galactosidase and a non-toxic ingestible excipient for said alpha-galactosidase, said composition being in tablet or soft-gel capsule form containing an amount of alpha-galactosidase effective to reduce such gastric distress, the ingesting of the composition being contemporaneous with the ingestion of the solid food containing said sugars.

18. A composition for reducing gastric distress in mammals due to ingestion of solid food containing alpha-D-galactoside-linked sugars, said composition containing alpha-galactosidase and a non-toxic ingestible excipient for said alpha-galactosidase, said composition being in tablet or soft-gel capsule form and containing an amount of alpha-galactosidase effective to hydrolyze said sugars in vivo to their simplest absorbable constituents after mixing in the stomach of the mammal ingesting the food.

19. The composition according to claim 18 wherein said composition further contains an agent for potentiating said alpha-galactosidase.

20. The composition according to claim 19, wherein said potentiating agent contains a blend of carbohydrases including arabanase, cellulase and xylanase.

21. A kit for reducing gastric distress in mammals due to ingestion of solid food containing alpha-D-galactoside-linked sugars, comprising a composition containing alpha-galactosidase and a non-toxic ingestible excipient for said alpha-galactosidase, said composition being in tablet or soft-gel capsule form and containing an amount of alpha galactosidase effective to hydrolyze said sugars in vivo to their simplest absorbable constituents after mixing in the stomach of the mammal ingesting the food, and instructions for ingesting the composition contemporaneously with the ingestion of the solid food containing said sugars.

* * * * *